United States Patent [19]

Eck et al.

[11] Patent Number: 5,130,252
[45] Date of Patent: Jul. 14, 1992

[54] RESOLUTION OF FUROPYRIDINE ENANTIOMERS AND SYNTHETIC PRECURSORS THEREOF

[75] Inventors: Charles R. Eck, Shrewsbury, Mass.; Paul C. Ahrens, Corvallis; Rae M. Saltzstein, McMinnville, both of Oreg.

[73] Assignee: Synthetech, Inc., Albany, Oreg.

[21] Appl. No.: 523,238

[22] Filed: May 14, 1990

[51] Int. Cl.$^5$ .............................. C12P 7/02
[52] U.S. Cl. ........................ 435/280; 435/118; 435/120; 435/122; 435/156
[58] Field of Search ............ 435/280, 118, 120, 122, 435/156

[56] References Cited

U.S. PATENT DOCUMENTS

| 4,916,074 | 4/1990 | Yoshida et al. | 435/135 X |
| 4,971,909 | 11/1990 | Kaneoya et al. | 435/280 |
| 4,985,365 | 1/1991 | Mitsuda et al. | 435/280 |
| 5,021,345 | 6/1991 | Urban et al. | 435/182 X |

FOREIGN PATENT DOCUMENTS

| 304706 | 3/1989 | European Pat. Off. | 435/122 |
| 216590 | 12/1984 | Japan | 435/155 |
| 224494 | 11/1985 | Japan | 435/156 |
| 289899 | 12/1986 | Japan | 435/156 |

Primary Examiner—Carolyn Elmore
Attorney, Agent, or Firm—Fish & Richardson

[57] ABSTRACT

A method for resolving racemic mixtures of compounds having the formula

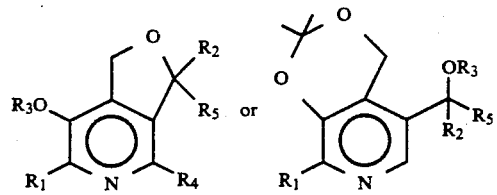

or a pharmaceutically acceptable salt thereof that includes the steps of reacting the $OR_3$ group of either compound with an esterifying agent in the case where $R_3$ is H or a lower alkyl group; sujecting the compound to the action of an esterase capable of preferentially hydrolyzing either the (+) or (−) enantiomeric form of the compound; and separating the unhydrolyzed compound from the hydrolyzed compound.

18 Claims, 2 Drawing Sheets

RESOLUTION OF FUROPYRIDINE ENANTIOMERS AND SYNTHETIC PRECURSORS THEREOF

BACKGROUND OF THE INVENTION

This invention relates to resolving racemic mixtures. ($\pm$)-3-(4-chlorophenyl)-1,3-dihydro- 7-hydroxy-6-methylfuro-[3,4-c]-pyridine is better known as Cicletanine, a diuretic and antihypertensive drug having the following formula:

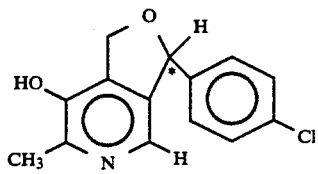

It exists as a synthetic racemate (the chiral carbon is denoted by an asterisk). It is believed that the biological activity of Cicletanine is associated predominantly with the [3R]-(−) enantiomer.

SUMMARY OF THE INVENTION

The invention features a method of resolving a racemic mixture of a compound having the formula

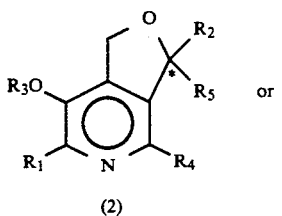 or 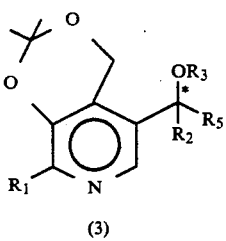

or a pharmaceutically acceptable salt thereof where $R_1$ is a branched or straight chain lower (e.g., $C_1$-$C_5$) alkyl or alkenyl group (e.g., methyl or isopropyl), either of which may be substituted with one or more hydroxyl, cyano, amino, substituted amino, or $C_1$-$C_4$ alkyl or alkenyl groups, or $R_1$ is a group having the formula

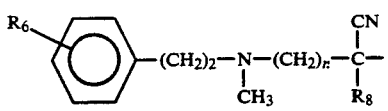

where n is an integer between 2 and 5, inclusive, $R_6$ represents from one to three methoxy groups, and $R_8$ is a branched or straight chain lower alkyl group (e.g., isopropyl);

$R_2$ and $R_5$, independently, are hydrogen, cyano, a straight chain saturated or unsaturated alkyl group preferably having between 1 and 5 carbon atoms, inclusive (e.g., methyl or vinyl); a 3-6 membered heterocyclic group (e.g., pyridyl or thienyl); a 3-6 membered cycloalkyl group (e.g., cyclohexyl); a phenyl, phenylalkyl (e.g., benzyl), or phenylalkenyl (e.g., vinylbenzyl) group, each of which may be substituted with one or more halogen (e.g., chlorine or fluorine), trifluoroalkyl (e.g., trifluoromethyl), lower alkyl (e.g., methyl), lower alkoxy (e.g., methoxy), lower thioalkyl (e.g., thiomethyl), dialkylamino (e.g., dimethylamino), dialkylaminoalkoxy (where both the alkyl and alkoxy groups have between 1 and 5 carbon atoms, inclusive, e.g, methyl or methoxy), or $\alpha$- or $\beta$-alkoxy N-pyrrolidinyl groups (e.g., pyrrolidinyl ethoxy phenyl); or a group having the formula

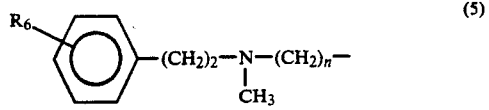

where n and $R_6$ are as recited above; provided that:
  i) $R_2$ is different from $R_5$; and
  ii) when one of $R_2$ or $R_5$ is cyano and the other is a group having the formula set forth in formula (5), then $R_1$ cannot be a group having the formula set forth in formula (4);

$R_3$ is H, a lower alkyl group (e.g., methyl), or

where $R_7$ is a lower alkyl group, e.g., methyl); and $R_4$ is H or a halogen group. The method includes the steps of:

reacting the $OR_3$ group of the compound with an esterifying agent (i.e., a reagent or group of reagents capable of reacting with the $OR_3$ group to convert it to an ester) in the case where $R_3$ is H or a lower alkyl group (i.e. the $OR_3$ group is not already in the form of an ester);

subjecting the compound to the action of an esterase capable of preferentially hydrolyzing either the (+) or (−) enantiomeric form of the compound; and separating the unhydrolyzed compound from the hydrolyzed compound.

In preferred embodiments, the esterifying agent is acetic anhydride. To separate the unhydrolyzed compound from the hydrolyzed compound, a solvent in which these compounds are differentially soluble is preferably used.

Preferred compounds are those in which $R_1$ is methyl, $R_2$ is p-chlorophenyl, $R_5$ is H, $R_3$ is H, and $R_4$ is H. Preferred esterases are selected form the group consisting of serine proteinase (EC 3.2.21), $\alpha$-chymotrypsin (EC 3.4.21.1), trypsin, lipase, wheat germ lipase (EC 3.1.1.3), and porcine pancrease lipase, with $\alpha$-chymotrypsin being the most preferred. The esterase preferably preferentially hydrolyzes the (−) enantiomeric form of the compound.

The invention provides a simple, effective, stereospecific method for resolving racemic mixtures. The method is particularly useful in preparing (-)- 3-(4-chlorophenyl)- 1,3-dihydro- 7-hydroxy-6-methylfuro [3,4-c]-pyridine (the biologically active form of the drug Cicletanine corresponding to compound (2) in which $R_1$ is methyl, $R_2$ is p-chlorophenyl, $R_5$ is H, $R_3$ is H, and $R_4$ is H) and (−)-2,2,8-trimethyl-5-(4-chloro-$\alpha$-hydroxybenzyl)-pyrido-[4,3e]-1,3-dioxane (a precursor useful in the asymmetric synthesis of (−)-3-(4-chlorophenyl)-1,3-dihydro-7-hydroxy-6-methylfuro-[3,4-c]-pyridine corresponding to compound (3) in which $R_1$ is methyl, $R_2$ is p-chlorophenyl, $R_5$ is H, $R_3$ is H, and $R_4$ is H).

Other features and advantages of the invention will be apparent from the following description of the preferred embodiments thereof, and from the claims.

DESCRIPTION OF THE PREFERRED EMBODIMENTS

We first briefly describe the drawings.

Drawings

Figure 1:
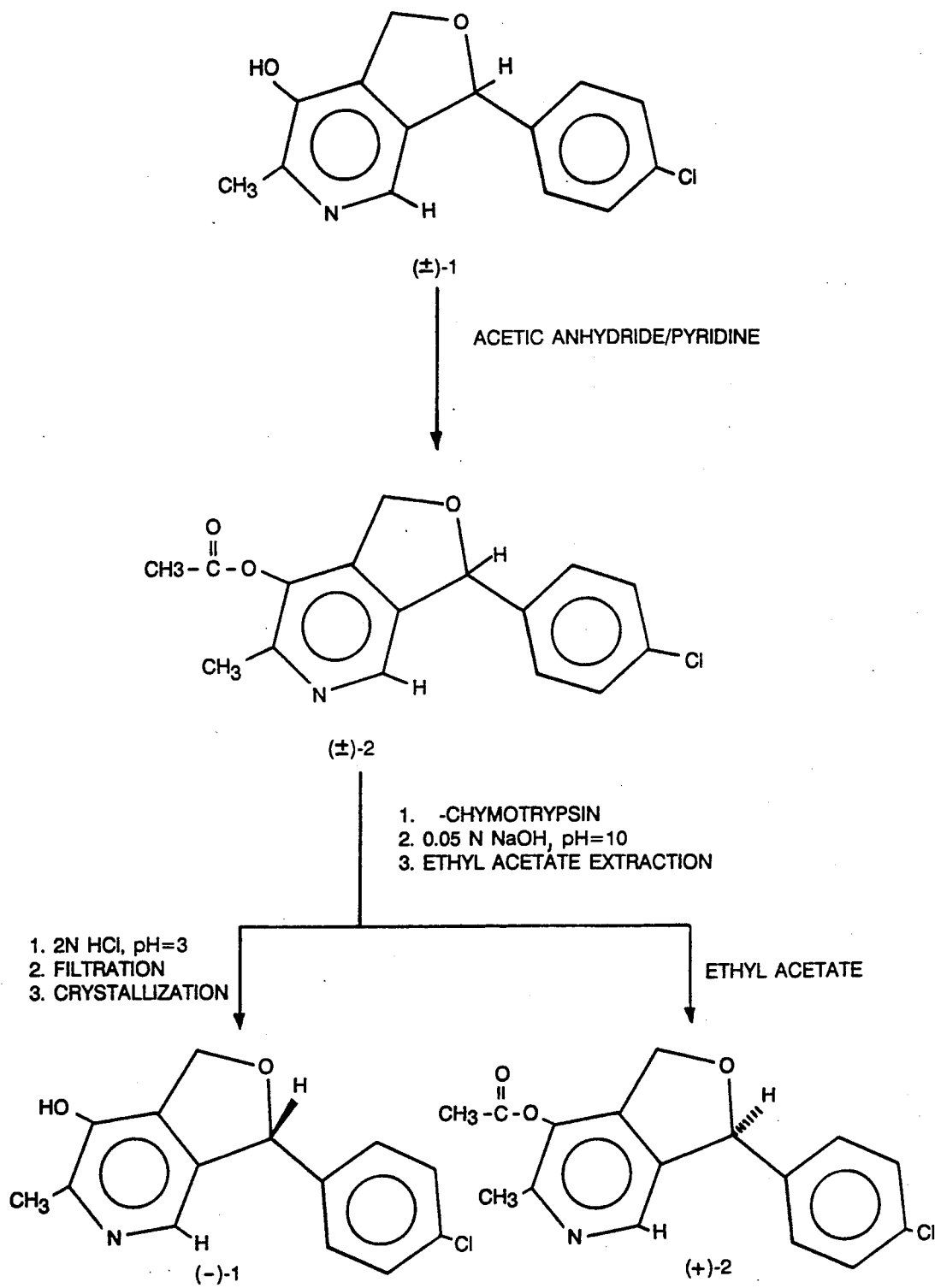
Figure 2:
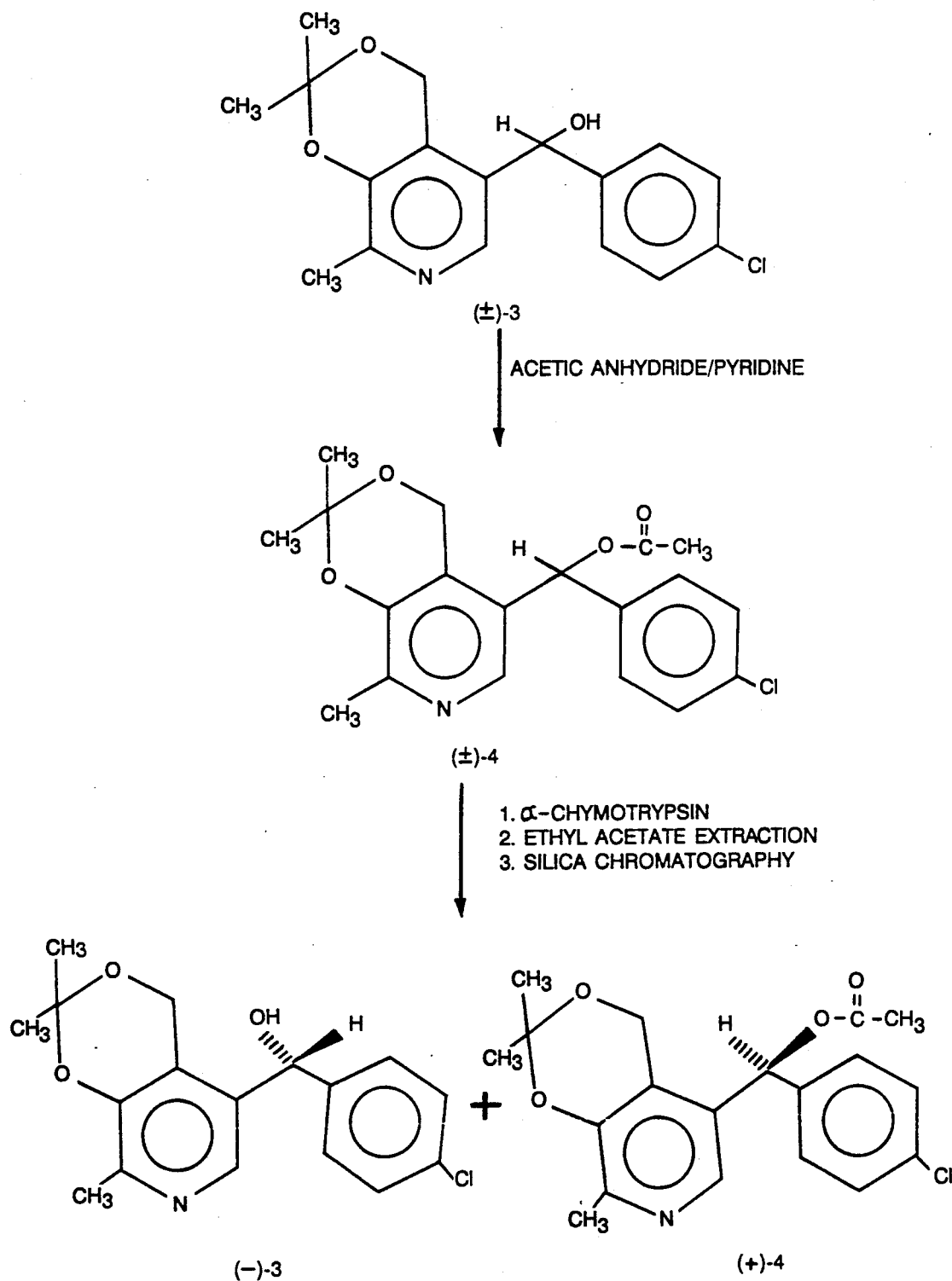

FIGS. 1 and 2 are flow charts illustrating the synthesis of (−)-3-(4-chlorophenyl)-1,3-dihydro-7-hydroxy-6-methylfuro-[3,4-c]-pyridine and (−)-2,2,8-trimethyl-5-(4-chloro-α-hydroxybenzyl)-pyrido-[4,3e]-1,3-dioxane, respectively.

REACTIONS

Referring to FIG. 1, the first step in the resolution of (±)-3-(4-chlorophenyl)-1,3-dihydro-7-hydroxy-6-methylfuro-[3,4-c]-pyridine ((±)-1) is to convert the hydroxyl group on the pyridine ring to an acetate ester ((±)-2). Next, (±)-2 is treated with α-chymotrypsin (EC 3.4.21.1) from bovine pancreas (commercially available from Sigma Chemicals) to hydrolyze the acetate group, thus regenerating the hydroxyl group. The hydrolysis reaction is stereospecific, hydrolysis of the (−) acetate enantiomer being preferred over hydrolysis of the (+) acetate enantiomer. Thus, at the end of the hydrolysis reaction (i.e. at the point where the hydrolysis reaction has proceeded to 50%, reflecting the fact that only the (−) enantiomer is hydrolyzed), the reaction mixture contains both hydrolyzed (−) ester ((−)-1) and unhydrolyzed (+) ester ((+)−2). These compounds are then separated by extracting the reaction mixture with a solvent such as ethyl acetate in which the unhydrolyzed (+) ester is more soluble than the hydrolyzed (−) ester.

Referring to FIG. 2, a similar approach is used to resolve (±)-2,2,8-trimethyl-5-(4-chloro-α-hydroxybenzyl)-pyrido-[4,3-e]-1,3-dioxane ((±)-3) via α-chymotrypsin catalyzed hydrolysis of the corresponding acetate ester ((±-4).

EXAMPLE 1

This example describes the resolution of (±)-3-(4-chlorophenyl)-1,3-dihydro-7-hydroxy-6-methylfuro-[3,4-c]-pyridine ((±) -1).

The extent of hydrolysis was determined using a Phenomenex 10 micron C-18 reverse phase high performance liquid chromatography column (30×3.9 mm). The mobile phase was an isocratic mixture of ammonium acetate (0.05 M, pH=4.5) and methanol (2:3) at a flow rate of 1.0 ml/minute. Detection was at 254 nm. (±)-1 eluted at approximately 4 minutes, while (±)-2 eluted at about 5 minutes.

The stereospecificity of the reaction was determined with a Chiralcel OJ high performance liquid chromatography column (25×0.46 cm). The mobile phase was a mixture of hexane and isopropyl alcohol (3:1) at a flow rate of 1.5 ml/minute. Detection was also at 254 nm. Under these conditions, the (−)−1 and (+)−1 enantiomers eluted at about 4 and 6 minutes, respectively. The (−)-2 and (+)-2 enantiomers eluted at 8 and 10 minutes, although the exact elution order is not known.

Synthesis of
(±)-3-(4-chlorophenyl)-1,3-dihydro-7-acetoxy-6-methylfuro-[3,4-c]-pyridine ((±)-2)

58 g of (±)-1 hydrochloride (0.2 mole) was placed in a 500 ml round bottom flask and covered with 175 ml of pyridine and 40 ml of acetic anhydride. The contents of the flask were then stirred at room temperature for 24 hours, after which they were poured into 500 ml of saturated sodium bicarbonate solution and stirred for 1 hour. A solid precipitate was formed. Next, the precipitate was suction filtered, washed with several volumes of water, and thorouqhly dried. The crude solid was then dissolved in 500 ml of methanol and set aside to crystallize. In this manner, 46 g of a homogeneous white solid shown to be (±)-2 was isolated.

Enzymatic hydrolysis of
(±)-3-(4-chlorophenyl)-1,3-dihydro
7-acetoxy-6-methylfure-[3,4-c]-pyridine ((±)-2)

300 mg of (±)-2 were dissolved in 30 ml of acetonitrile and then added to an Erlenmeyer flask containing 3 g of α-chymotrypsin (Sigma, C4129) in 270 ml of 0.05 phosphate buffer (pH=7). The incubation mixture was then stirred at room temperature for 3 hours to allow the hydrolysis reaction to proceed.

Isolation of
(−)-3-(4-chlorophenyl)-1,3-dihydro-7-hydroxy-6-methylfuro−[3,4-c]-pyridine ((−)-1)

Following enzymatic hydrolysis, the α-chymotrypsin was filtered off and the pH of the filtrate adjusted to 10 with 0.2 N NaOH. The aqueous solution was then extracted with ethyl acetate (3×100 ml); the unhydrolyzed (+)-2 ester was preferentially extracted into the organic phase. Next, the pH of the aqueous phase was adjusted to 3 with 2 N HCl and the precipitated solid (100 mg) collected by suction filtration. Recrystallization of the crude solid from methanol gave 75 mg of (−)-1, as determined by the high performance liquid chromatography procedure described above.

EXAMPLE 2

This example describes the resolution of (±)- 2,2,8-trimethyl- 5-(4-chloro-α-hydroxybenzyl)-pyrido -[4,3-e]-1,3-dioxane ((±)-3). The extent of hydrolysis was measured as described in Example 1. The acetate ester ((±)-4) eluted at about 9 minutes, while the alcohol ((±)-3) eluted at about 5.5 minutes. The stereospecificity was also measured as in Example 1 except that a flow rate of 0.25 ml/minute was used. Under these conditions, the (−)-3 and (+)-3 enantiomers eluted at about 22 and 24 minutes, respectively. The (−)-4 and (+)-4 enantiomers eluted at 25 and 30 minutes, although the exact elution order is not known.

(±)-3 was prepared from the corresponding alcohol as in Example 1. Next, 10 g of (±)-3 was dissolved in 200 ml of acetone and added to an Erlenmeyer flask containing 10 g of α-chymotrypsin (Sigma, C-4129) in 1800 ml of 0.05 M phosphate buffer (pH=7.0). The reaction mixture was then stirred for 24 hours at room temperature, after which the acetone was removed by rotary evaporation and the remaining aqueous solution extracted with ethyl acetate (3×500 ml). After drying the ethyl acetate over sodium sulfate and removing the solvent by rotary evaporation, the crude solid (ca 9 g) was redissolved in a mixture of methylene chloride (20 ml) and methanol (5.0 ml), loaded on top of a silica gel column (150 g), and eluted with methylene chloride/-methanol (98:2). Two discrete fractions were collected and shown to be (−)-3 (3.5 g) and (+)- 4 (3.2 g).

Other embodiments are within the following claims.

For example, preparations involving enzymes other than α-chymotrypsin and/or different racemic mixtures are carried out using procedures similar to those described above.

We claim:

1. A method of resolving a racemic mixture of a compound with a chiral center having the following formula in which said chiral center is denoted by an asterisk

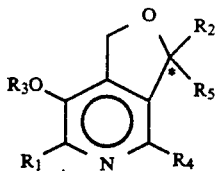

or a pharmaceutically acceptable salt thereof where $R_1$ is a branched or straight chain lower alkyl or alkenyl group, either of which may be substituted with one or more hydroxyl, cyano, amino, or substituted amino, or $R_1$ is a group having the formula

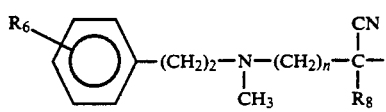

where n is an integer between 2 and 5, inclusive, $R_6$ represents from one to three methoxy groups, and $R_8$ is a branched or straight chain lower alkyl group;

$R_2$ and $R_5$, indepenently, are hydrogen; cyano; a straight chain saturated or unsaturated alkyl group; a 3-6 membered heterocyclic group; a 3-6 membered cycloalkyl group; a phenyl, phenylalkyl, or phenylalkenyl group, each of which may be substituted with one or more halogen, trifluoroalkyl, lower alkyl, lower alkoxy, lower thioalkyl, dialkylamino, dialkylaminoalkoxy, or α- or B-alkoxy N-pyrrolidinyl groups; or a group having the formula

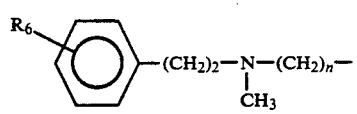

where n is an integer between 2 and 5, inclusive, and $R_6$ represents from one to three methoxy groups, provided that:

i) $R_2$ is different from $R_5$; and
ii) when one of $R_2$ or $R_5$ is cyano and the other is a group having the formula

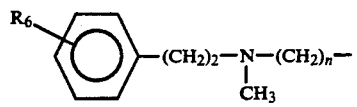

then $R_1$ cannot be a group having the formula

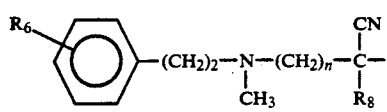

$R_3$ is H or $R_7C$- where $R_7$ is a lower alkyl group; and $R_4$ is H or a halogen group;

said method comprising the steps of:
reacting the $OR_3$ group of said compound with an esterifying agent in the case where $R_3$ is H;
subjecting said compound to the action of an esterase capable of preferentially hydrolyzing either the (+) or (−) enantiomeric form of said compound; and
separating the unhydrolyzed compound from the hydrolyzed compound.

2. The method of claim 1 wherein said esterifying agent is acetic anhydride.

3. The method of claim 1 wherein said separating step comprises extracting the products of the hydrolysis treatment with a solvent in which the hydrolyzed compound and unhydrolyzed compound are differentially soluble.

4. The method of claim 1 wherein $R_1$ is methyl, $R_2$ is p-chlorophenyl, $R_5$ is H, $R_3$ is H, and $R_4$ is H.

5. The method of claim 1 wherein said esterase is selected from the group consisting of serine proteinase, α-chymotrypsin, trypsin, lipase, wheat germ lipase, and porcine pancreas lipase.

6. The method of claim 5 wherein said esterase is α-chymotrypsin.

7. The method of claim 1 wherein said esterase preferentially hydrolyzes the (−) enantiomeric form of said compound.

8. A method of resolving a racemic mixture of a compound with a chiral center having the following formula in which said chiral center is denoted by an asterisk

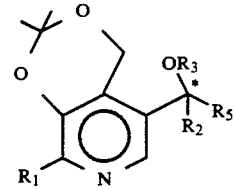

(3)

or a pharmaceutically acceptable salt thereof wherein $R_1$ is a branched or straight chain lower alkyl or alkenyl group, either of which may be substituted with one or more hydroxyl, cyano, amino, or substituted amino, or $R_1$ is a group having the formula

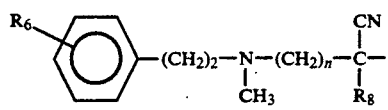

where n is an integer between 2 and 5, inclusive, $R_6$ represents from one to three methoxy groups, and $R_8$ is a branched or straight chain lower alkyl group;

$R_2$ and $R_5$, independently, are hydrogen; cyano; a straight chain saturated or unsaturated alkyl group; a 3-6 membered heterocyclic group; a 3-6 membered cycloalkyl group; a phenyl, phenylalkyl, or phenylalkenyl group, each of which may be substituted with one or more halogen, trifluoroalkyl, lower alkyl, lower alkoxy, lower thioalkyl, dialkylamino, dialkylaminoalkoxy, or α- or B-alkoxy N-pyrrolidinyl groups; or a group having the formula

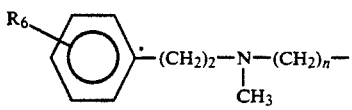

where n is an integer between 2 and 5, inclusive, and $R_6$ represents from one to three methoxy groups,
provided that:
  i) $R_2$ is different from $R_5$ and at least one of $R_2$ and $R_5$ contains a cyclic or aromatic group; and
  ii) when one of $R_2$ or $R_5$ is cyano and the other is a group having the formula

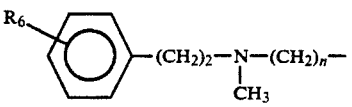

then $R_1$ cannot be a group having the formula

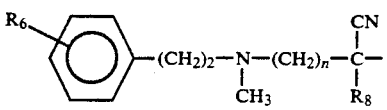

$R_3$ is H or $R_7$C-where $R_7$ is a lower alkyl group; and
$R_4$ is H or a halogen group;
reacting the $OR_3$ group of said compound with an esterifying agent in the case where $R_3$ is H;
subjecting said compound to the action of an esterase capable of preferentially hydrolyzing either the (+) or (−) enantiomeric form of said compound; and
separating the unhydrolyzed compound from the hydrolyzed compound.

9. The method of claim 8 wherein said esterifying agent is acetic anhydride.

10. The method of claim 8 wherein said separating step comprises extracting the products of the hydrolysis treatment with a solvent in which the hydrolyzed compound and the unhydrolyzed compound are differentially soluble.

11. The method of claim 8 wherein $R_1$ is methyl, $R_2$ is p-chlorophenyl, $R_3$ is H, and $R_4$ is H.

12. The method of claim 8 wherein said esterase is selected from the group consisting of serine proteinase, α-chymotrypsin, trypsin, lipase, wheat germ lipase, and porcine pancreas lipase.

13. The method of claim 12 wherein said esterase is α-chymotrypsin.

14. The method of claim 8 wherein said esterase preferentially hydrolyzes the (−) enantiomeric form of said compound.

15. The method of claim 1 wherein at least one of $R_2$ and $R_5$ is H.

16. The method of claim 15 wherein at least one of $R_2$ and $R_5$ contains an aromatic group.

17. The method of claim 8 wherein at least one of $R_2$ and $R_5$ is H.

18. The method of claim 17 wherein at least one of $R_2$ and $R_5$ contains an aromatic group.

* * * * *

UNITED STATES PATENT AND TRADEMARK OFFICE
CERTIFICATE OF CORRECTION

PATENT NO. : 5,130,252           Page 1 of 2
DATED      : July 14, 1992
INVENTOR(S): Charles R. Eck, et al It is certified that error appears in the above-indentified patent and that said Letters Patent is hereby corrected as shown below:

Item [57] ABSTRACT, after the formula, line 4, "sujecting" should read --subjecting--

Col. 2, line 45, change "form the group" to --from the group--;

Col. 4, line 12 of the heading, change "-6-methylfure-" to -- -6-methylfuro- --;

Col. 5, claim 1, line 66, change "$R^7C-$" to -- $R^7\overset{O}{\underset{\|}{C}}-$ ;

Column 7, claim 8, line 29, change "$R^7$" to --$R_7-\overset{O}{\underset{\|}{C}}$---

UNITED STATES PATENT AND TRADEMARK OFFICE
CERTIFICATE OF CORRECTION

PATENT NO. : 5,130,252
DATED : July 14, 1992
INVENTOR(S) : Charles R. Eck, et al It is certified that error appears in the above-indentified patent and that said Letters Patent is hereby corrected as shown below:

Col. 7, claim 8, 31, delete "$R_4$ is H or a halogen group;" and insert instead --said method comprising the steps of: --.

Signed and Sealed this

Seventh Day of December, 1993

*Attest:*

BRUCE LEHMAN

*Attesting Officer*  *Commissioner of Patents and Trademarks*